US009999367B2

(12) United States Patent
Vullings et al.

(10) Patent No.: US 9,999,367 B2
(45) Date of Patent: Jun. 19, 2018

(54) FETAL CARDIOTOCOGRAPHY MONITORING

(71) Applicant: Technische Universiteit Eindhoven, Eindhoven (NL)

(72) Inventors: Rik Vullings, Venray (NL); Swan Gie Oei, Veldhoven (NL)

(73) Assignee: Technische Universiteit Eindhoven, Eindhoven (NL)

( * ) Notice: Subject to any disclaimer, the term of this patent is extended or adjusted under 35 U.S.C. 154(b) by 63 days.

(21) Appl. No.: 15/352,781

(22) Filed: Nov. 16, 2016

(65) Prior Publication Data
US 2017/0055866 A1     Mar. 2, 2017

Related U.S. Application Data

(63) Continuation-in-part of application No. 14/672,925, filed on Mar. 30, 2015, now abandoned.

(60) Provisional application No. 61/972,536, filed on Mar. 31, 2014, provisional application No. 62/140,010, filed on Mar. 30, 2015.

(51) Int. Cl.
| | |
|---|---|
| *A61B 5/0444* | (2006.01) |
| *A61B 5/0452* | (2006.01) |
| *A61B 5/044* | (2006.01) |
| *A61B 5/00* | (2006.01) |
| *A61B 5/04* | (2006.01) |

(52) U.S. Cl.
CPC ............ *A61B 5/0444* (2013.01); *A61B 5/044* (2013.01); *A61B 5/04012* (2013.01); *A61B 5/0452* (2013.01); *A61B 5/4362* (2013.01); *A61B 5/7282* (2013.01); *A61B 5/746* (2013.01); *A61B 5/7435* (2013.01)

(58) Field of Classification Search
CPC ... A61B 5/0444; A61B 5/0468; A61B 5/4343; A61B 5/4362; A61B 5/7275; A61B 5/7282; A61B 5/746
See application file for complete search history.

(56) References Cited

PUBLICATIONS

"ST Analysis—Clinical Bibliography". <http://www.neoventa.com/st-analysis-clinical-bibliography>. Accessed Mar. 31, 2018.*
"Dr.ir. R. (Rik) Vullings—Publications". <https://www.tue.nl/en/university/departments/electrical-engineering/department/staff/detail/ep/e/d/ep-uid/19981523/ep-tab/4/>. Accessed Mar. 31, 2018.*
"Prof.dr. S.G. (Guid) Oei—Publications". <https://www.tue.nl/en/university/departments/electrical-engineering/department/staff/detail/ep/e/d/ep-uid/20031643/ep-tab/4/>. Accessed Mar. 31, 2018.*
Hulsenboom, A.D.J., Vullings, R, Van Laar, J.O.E.H., Van Der Hout-Van Der Jagt, M.B. & Oei, S.G. (2014). How to improve ST-analysis in fetal monitoring: Relative versus absolute t/qrs ratio rises. Journal of Maternal-Fetal and Neonatal Medicine, 27(suppl. 1), 191-192.*
Comparison of Morphological Characteristics Between Invasive and Non-invasive Foetal Electrocardiograms, University of Oxford Master Thesis, Aug. 27, 2010.

(Continued)

*Primary Examiner* — Eugene T Wu
(74) *Attorney, Agent, or Firm* — Lumen Patent Firm

(57) ABSTRACT

An improved fetal ST monitoring system and method is provided using an ECG monitoring system collecting a plurality of T/QRS segments of a fetus, and a data analysis computer system connected to the ECG monitoring system calculating from the plurality of T/QRS segments.

2 Claims, 4 Drawing Sheets

(56) References Cited

PUBLICATIONS

Detection of the abdominal fetal electrocardiogram: A study into changes in the optimal recording sites during gestation and the evaluation of non-contact sensors, Technical University Eindhoven Master Thesis, Dec. 2005.

* cited by examiner

FETAL CARDIOTOCOGRAPHY MONITORING

CROSS-REFERENCE TO RELATED APPLICATIONS

This application is a continuation-in-part of U.S. patent application Ser. No. 14/672,925 filed Mar. 30, 2015, which is incorporated herein by reference. U.S. patent application Ser. No. 14/672,925 filed Mar. 30, 2015 claims priority from U.S. Provisional Patent Applications 61/972,536 filed Mar. 31, 2014 and 62/140,010 filed Mar. 30, 2015, which are incorporated herein by reference.

FIELD OF THE INVENTION

This invention relates to fetal monitoring. In particular, the invention relates to fetal cardiotocography (CTG) monitoring.

BACKGROUND OF THE INVENTION

Reducing infant mortality and morbidity is one of the major challenges of modern healthcare. Analysis of the fetal electrocardiogram ST segment was once believed to be the Holy Grail in fetal monitoring, but its implementation in clinical practice yields many false alarms, limiting its value for predicting fetal distress.

SUMMARY OF THE INVENTION

A fetal ST monitoring system and method are provided using an ECG monitoring system for collecting a plurality of T/QRS segments of a fetus. A data analysis computer system connected to the ECG monitoring system calculates alarms from the plurality of T/QRS segments.

The computer system determines a first alarm of a first compromised condition of the fetus. The first alarm is triggered as a first ratio of two different baseline features of the T/QRS segments exceeding a first threshold. The computer system determines a second alarm of a second compromised condition of the fetus. The second alarm is triggered as a second ratio of an episodic feature of the T/QRS segments and one of the baseline features exceeding a second threshold. The computer system displays information of the first alarm and/or the second alarm which when exceeding their respective thresholds is a measure to trigger a medical intervention. The display of the alarm(s) does not rely on or does not include a cardiotocography (CTG) classification or measurement.

The embodiments of the invention is an improvement of the STAN monitor method and system.

DETAILED DESCRIPTION

Figure 1:
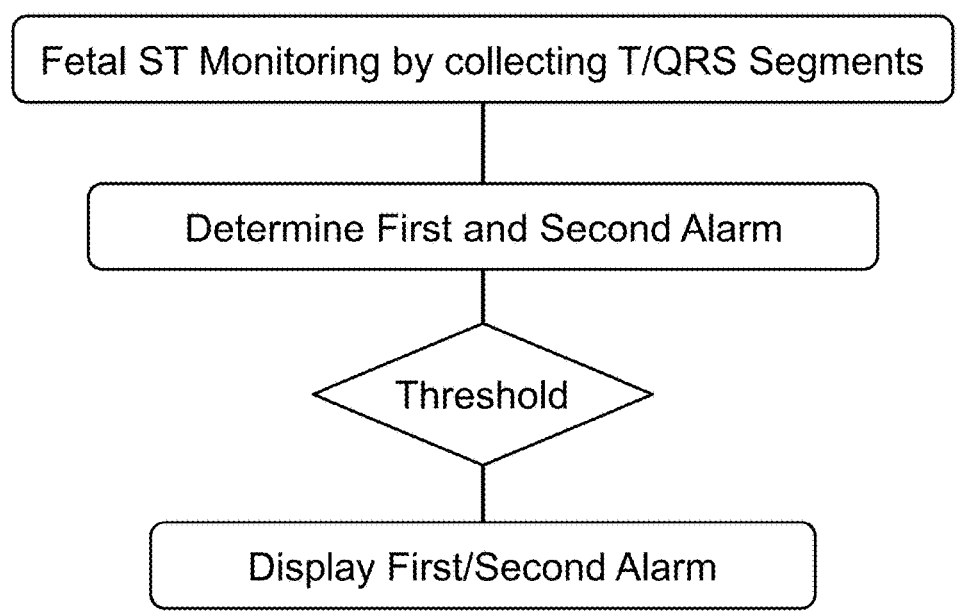
FIG. 1 shows according to an exemplary embodiment of the invention a schematic method of fetal ST monitoring using an ECG monitoring system collecting a plurality of T/QRS segments of a fetus, and a data analysis computer system connected to the ECG monitoring system calculating from the plurality of T/QRS segments.

The present invention of relative ST analysis is an improved methodology of fetal ST analysis as it is currently performed by the STAN monitor (Neoventa, Moelndal, Sweden).

The STAN monitor uses a fetal scalp electrode (an invasive electrode typically connected to the fetal head) to record a fetal ECG. The fetal ECG is subsequently processed by the STAN monitor via a series of signal processing and feature extraction steps. Next, based on the extracted features alarms can be generated that should be related to pending fetal distress (due to lack of or insufficient oxygen). The present invention relates to the interpretation of the extracted features and the way alarms should be generated based on these features.

Signal Processing

When the fetal ECG is recorded, this signal is contaminated by various interferences (e.g. powerline grid). To enhance signal quality, STAN employs a series of filters, signal averaging and curve fitting. In the signal averaging, STAN waits until 30 ECG complexes have been recorded (and filtered) that satisfy certain criteria regarding signal quality. As soon as 30 ECG complexes are accepted, an averaged ECG waveform is created. This averaged waveform is subsequently (post) processed using curve fitting to further enhance signal quality. The goal of averaging is also to enhance the signal. Noise that is temporally uncorrelated to the ECG could be reduced upon averaging.

The averaged and post-processed ECG waveform is used as input in the feature extraction algorithms. Feature extraction hence only occurs after 30 individual ECG complexes have been accepted. Assuming good signal quality (so acceptance of virtually all ECG complexes) and a fetal heart rate of 140 beats-per-minute, an averaged ECG waveform is generated every 12.8 seconds.

Feature Extraction

The feature of primary interest in STAN's ST analysis is the amplitude of the ECG's T-wave. This amplitude is defined as the maximum deflection of the T-wave with respect to the ECG's baseline (which is ideally obtained from the isoelectrical period between P and R waves). The exact method that STAN uses to determine the ECG baseline is unknown.

To compensate for inter-patient differences in ECG signal strength, the amplitude of the T-wave is normalized against the QRS amplitude (distance between maximum and minimum amplitude of QRS complex), yielding the T/QRS ratio. So, the T/QRS ratio is determined after every 30 accepted heartbeats and represents the normalized T-wave amplitude in an averaged ECG waveform.

Alarm Generation

The T/QRS ratio serves as input to the alarm mechanism. Before describing details of the alarm mechanism, let's first discuss the three types of alarms that STAN can give:
  Baseline T/QRS rise: defined as a rise in T/QRS that occurs slowly and in which T/QRS elevation lasts at least 10 minutes.
  Episodic T/QRS rise: defined as a short-term rise in T/QRS and for which the T/QRS values return to their baseline within 10 minutes.
  Biphasic ST segment: not relevant for our current study and unrelated to the T/QRS ratio.

To determine whether baseline or episodic T/QRS rises occur, STAN uses a small number of parameters, defined as:
  Individual T/QRS value: the T/QRS values as defined above: the ratio between T-wave amplitude and QRS amplitude determined in an averaged ECG waveform (averaged from 30 accepted ECG complexes).

The following parameters are determined once every minute. When index i indicates the current time-instant/minute, then the parameters are defined as follows.
  B10(i): the median of all individual T/QRS ratios within a 10-minute window preceding i. B10 is only determined when this 10-minute window contains at least 10 individual T/QRS ratios. When signal quality was poor and many ECG complexes were rejected and thus not included in the averaging, it can occur that not enough T/QRS ratios are determined in the 10-minute window.
  B20(i): the median of all individual T/QRS ratios within a 20-minute window preceding i. B20 is only determined when this 20-minute window contains at least 20 individual T/QRS values.
  MB20(i): the minimum value of B20 within a 3-hour window preceding i. In case not enough "history" is present, the 3-hour window is defined as the window between the start of the recording and time i−1.
  BaselineRise(i): the difference between B10(i) and MB20(i)
  EpisodicRise(i): the difference between the largest individual T/QRS ratio that was determined in minute i and B10(i).

STAN generates an alarm when BaselineRise(i) exceeds 0.05 and/or when EpisodicRise(i) exceeds 0.10.

Improvements of the Present Invention

Based on our physiological explanation of false ST events (see infra Addendum), a major improvement might be achievable when the parameters BaselineRise(i) and EpisodicRise(i) are defined differently.

For the solution, BaselineRise(i) should be defined as the ratio between B10(i) and MB20(i) (and alarms generated when this ratio exceeds, for example, but not limited to 0.7) and EpisodicRise(i) should be defined as the ratio between the maximum individual T/QRS in minute i and B10(i) (and alarms generated when this ratio exceeds, for example, but not limited to 0.7).

As indicated in the Addendum, we have tested our solution for a small number of patients, but already saw large potential. However, we also ran into a problem for which the optimal solution has not yet been found. When dealing with ratios, it can happen that the denominator is zero (MB20(i) in case of BaselineRise or B10(i) in case of EpisodicRise). When this happens the rise would be infinite and always exceed any possible threshold and thus yield an alarm. Until now, we have solved this by replacing the zero-value of MB20(i) (or similarly for B10(i)) by the last determined value that was not equal to zero. Others solutions can also be considered, e.g. when determining B10(i) and/or B20(i) and these would be zero, exclude the extreme individual T/QRS values in the corresponding window and see whether this changes the median to a non-zero value.

Besides using the definitions above (BaselineRise(i) as ratio between B10(i) and MB20(i) and EpisodicRise(i) as ratio between maximum individual T/QRS and B10(i)), we have also experimented with other ratios, e.g. between B5, B10, B15, B20, B30 and MB5, MB10, etc. (all with definitions analogue to the definitions by STAN) and we have also tested completely different definitions (e.g. not the median over a x-minute window, but just the median over the last x-values). Some combinations performed worse in giving accurate alarms (e.g. B30/MB5, in line with our expectations), but in general the difference between our method and the STAN method really was due to the fact that we used ratios (B_x/MB_y) instead of absolute differences (B_x-MB_y).

Significance of Improvement

For our study towards the significance of the improvement, we tested this by using the same features as STAN: B10, MB20, individual T/QRS. So our BaselineRise(i) was B10(i)/MB20(i) and EpisodicRise(i) was ratio between maximum individual T/QRS in minute i and B10(i).

We used a case-control study with 10 healthy cases (pH>7.20) and 10 patients born with pH<7.05 (which is really a poor condition of the fetus). pH is here determined from the umbilical artery.

The STAN monitor gave alarms with sensitivity of 90% (so for 9 out of the 10 cases with pH<7.05 an alarm was generated) and a specificity of 40% (so for 6 out of 10 healthy cases an alarm was also triggered). The improved method of this invention for the same group yielded sensitivity of 90% (so 1 case of low pH for which no alarm was triggered) and specificity of 100% (no alarms were triggered in the healthy group).

In the method of the present invention, the displaying of the alarm(s), and/or the analysis/interpretation is based on ST monitoring and do not rely of any additional CTG classification. In fact, our method could solely rely on ST monitoring using relative ST events rather than absolute ST events with added CTG classification, with the method of the present invention resulting in a significant improvement of specificity from 40% to 100% (comparing the method of the present invention to the STAN method) without loss of sensitivity, i.e. no false positive alarms without additional false negative alarms.

Addendum: Explanation of Unsatisfactory STAN Alarms

Our explanation of the unsatisfactory STAN alarms not only entails the occurrence of alarms in case the fetal condition is uncompromised, but also includes those cases where the fetal condition is compromised but no alarms are raised. We will refer to both cases as the incidence of false alarms.

We will show that STAN alarms are related to normal variations in the behavior of the heart. More particularly, we will show that the orientation of the electrical axis of the heart is of vital importance to the incidence of STAN alarms. Each contraction of the cardiac muscle is initiated by the propagation of an electrical current across the cardiac muscle cells. We can measure these currents from the outside as an electrocardiogram (ECG). The main direction of propagation is referred to as the electrical axis of the heart and is also the direction in which we can record the largest ECG signal.

It is known that in adults the orientation of the electrical heart axis varies from person to person. This is also demonstrated for (preterm) neonates. But to substantiate our hypothesis that variations in the orientation of the electrical heart axis are the root cause of false STAN alarms, we have to make sure these variations also apply to the prenatal situation. To this end, we conducted non-invasive fetal electrocardiographic recordings with adhesive electrodes on the maternal abdomen in fetuses with gestational age of 20-28 weeks. Using dedicated signal processing methods, we isolated the fetal cardiac activity from the recorded biopotential signals and determined the direction in which the fetal ECG showed the largest amplitude. Based on simultaneously performed ultrasound imaging analysis, we were able to determine the position of the fetus in the uterus. Subsequently, we mapped the direction of largest ECG amplitude onto the fetal heart, yielding an estimate for the orientation of the fetal electrical heart axis.

Figure 2:
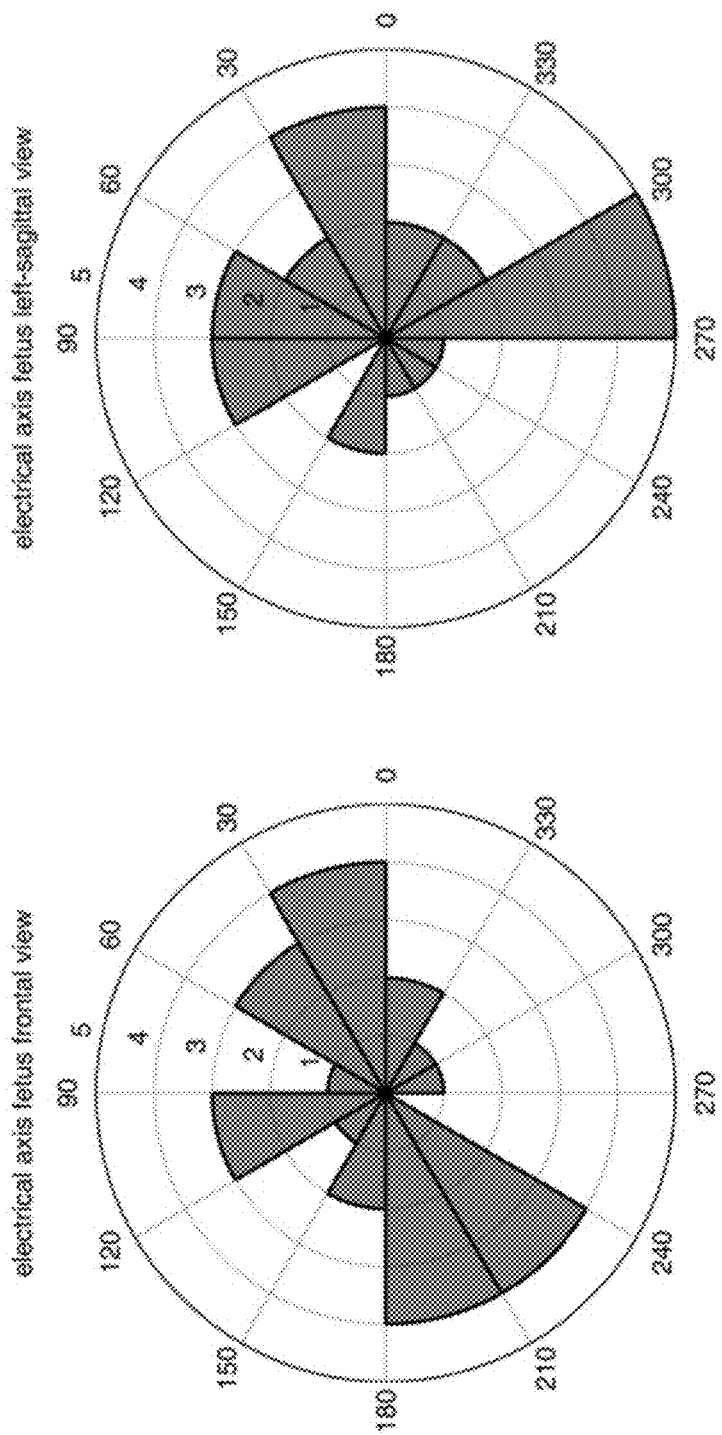
FIG. 2 shows according to an exemplary embodiment of the invention histograms of the orientation of the electrical heart axis for 26 healthy fetuses. The left histogram shows the frontal plane of the fetal body. The right histogram shows the left-sagittal plane. p-Values (null-hypothesis) for the provided results are $p<0.05$.

In FIG. 2, the orientation of the electrical heart axis is presented for a study population of 26 healthy fetuses with age ranging between 20 and 28 weeks of gestation. The absence of severe cardiac malformations was confirmed after birth. All patients signed written informed consent. From these results, two conclusions can be drawn: 1) The orientation of the heart axis varies significantly between fetuses. 2) The most common orientation of the electrical axis of the fetal heart is towards the right-posterior-inferior octant. This is in line with previous studies in the newborn infant. The difference with respect to the adult case, where the heart axis is oriented towards the left, can be explained by differences between the prenatal and postnatal hemodynamic circulations.

The Result: False Alarms by the Patient Monitor

According to the physiological (animal) studies preceding the introduction of the STAN monitor, sustained deprivation of oxygen is followed by a surge of adrenalin to induce glycogenolysis. This glycogenolysis is accompanied by an increase of potassium ions in the myocard. These potassium ions mainly affect the relaxation phase of the cardiac cycle and lead to an increase in the T-wave amplitude of the fetal ECG.

STAN exploits this hypoxia-related rise in T-wave amplitude via a three-step protocol. In the first step, the T-wave amplitude is normalised against the amplitude of the QRS-complex (i.e. the ventricular contraction phase of the cardiac cycle), yielding a T/QRS value. In the second step, a baseline for the T/QRS values is determined to gauge future T/QRS values. In the third step, newly determined T/QRS values are compared to the baseline. In case a T/QRS value exceeds the baseline by 0.05, an alarm is raised. Smaller exceeding of the baseline can be due to normal beat-to-beat fluctuation in the behavior of the heart, which is unrelated to the fetal condition, and is hence ignored. With regard to the detection of rises in T-wave amplitude due to oxygen deprivation, this alarm protocol sound rather plausible. However, in our opinion one vital concept was overlooked while defining this protocol.

Figure 3:
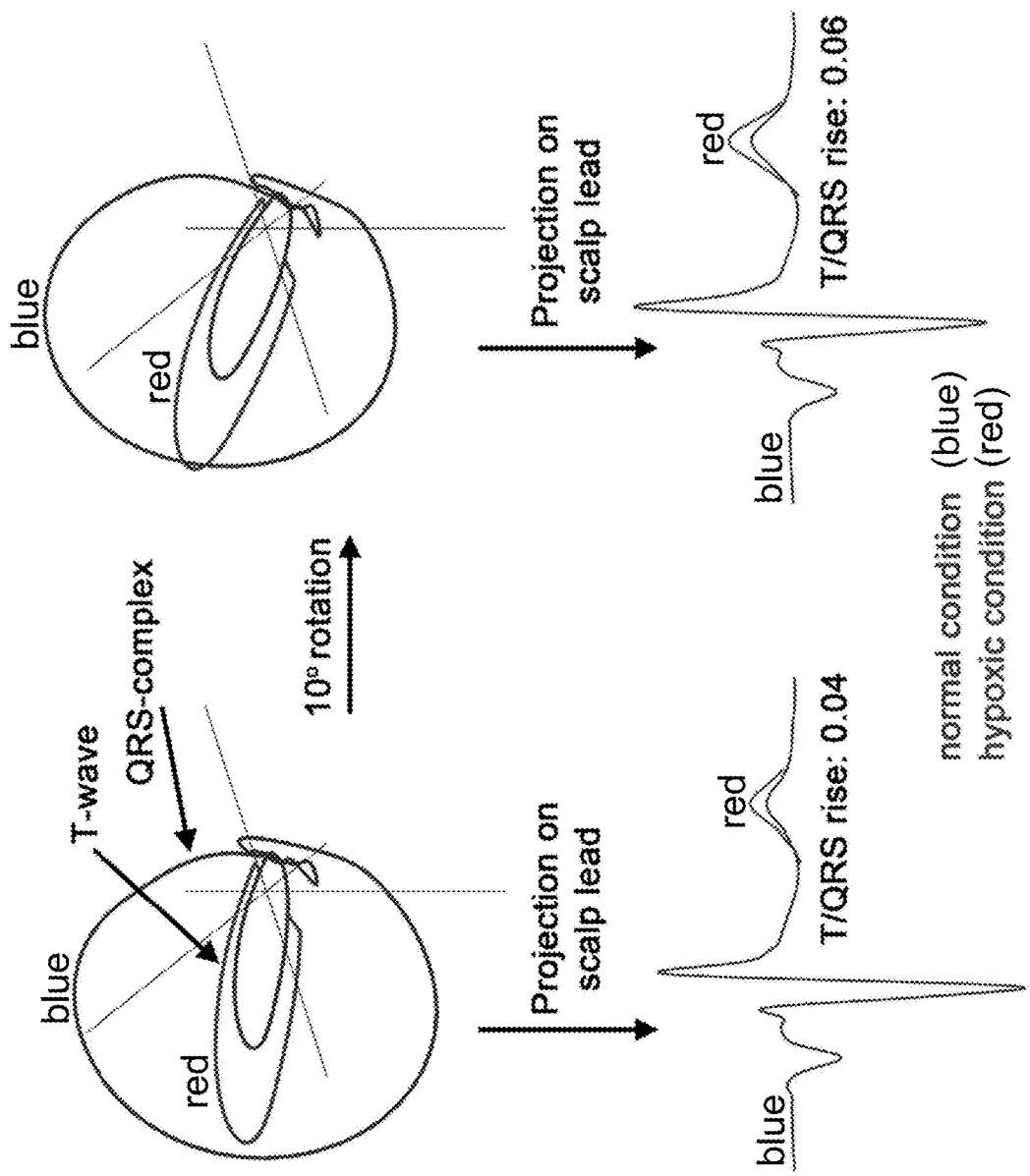
FIG. 3 shows according to an exemplary embodiment of the invention, in the top panels, the electrical currents within the heart during a cardiac cycle are depicted in terms of their vectorcardiogram. The large loops represent the activity during contraction of the ventricles: the QRS-complexes. The smaller loops represent the relaxation phase (T-waves). In blue, the heart is depicted under normal conditions. In red the heart is depicted when operating under lack of oxygen (hypoxia). From left to right, the entire vectorcardiogram, including both loops, has been rotated over 10 degrees to simulate different orientation of the electrical heart axis. In the bottom panels, the fetal scalp ECG has been calculated by projecting the vectorcardiograms onto the scalp lead (here: vertical axis). Before rotation, the baseline T/QRS is 0.05 and the T/QRS rise resulting from hypoxia is 0.04, yielding no STAN alarm. After rotation, the baseline T/QRS is 0.09 and the T/QRS rise is 0.06, yielding a STAN alarm. The depicted vectorcardiograms are a 2-dimensional projection of a 3-dimensional loop. The shape of the vectorcardiograms might hence look different, but it should the noted that these are exactly the same. Colors have been converted to gray scale.

The ECG recorded from the fetal scalp is a one-dimensional presentation of the electrical activity of the heart. In its simplest form, however, the propagation of electrical currents over the cardiac muscle occurs in all three spatial dimensions. The orientation of the electrical heart axis with respect to the fetal scalp hence affects the shape and amplitude of the ECG. Similarly, ECG signals recorded at different locations yield different shapes and amplitudes. STAN tries to account for this effect by the first step in its protocol (i.e. normalisation of the T-wave amplitude against the QRS-complex). However, the propagation of the electrical currents during the contraction (QRS) phase of the cardiac cycle has a different orientation than during the relaxation (T) phase. Consequently, this normalisation is only a crude attempt to account for inter-patient differences in the orientation of the electrical heart axis. As a result, fetuses for which the scalp lead is almost perpendicular to the direction of propagation in the relaxation phase have a very small T-wave amplitude, and typically also small T/QRS values. Similarly, fetuses for which the electrical heart axis is oriented such that the propagation during relaxation is almost aligned with the scalp lead typically have a large T/QRS ratio. Now, when the electrical currents in the relaxation phase are affected by hypoxia-induced release of potassium, for the fetuses with a small T/QRS ratio, the absolute effect in T-wave amplitude will only be marginal as we are looking at it from an almost perpendicular direction. For fetuses with high T/QRS values, the rise in T-wave amplitude will be relatively large. In FIG. 3, we explain this phenomenon.

Based on the reasoning above, we can hypothesise that normal fluctuations in the electrophysiological behavior of the heart can easily exceed the 0.05 threshold, as long as the alignment between the electrical heart axis and scalp lead is appropriate. Similarly, we can hypothesise that hypoxia-related fluctuations in the electrical behavior stay below the 0.05 threshold in case the scalp lead is oriented more perpendicular to the relaxation currents, as also shown in the left panel of FIG. 3. In short, we hypothesise that the STAN monitor raises more alarms for fetuses that have a high T/QRS baseline and fewer alarms for fetuses with a low baseline.

To attribute our hypothesis to variations in the orientation of the electrical heart axis and not to hypoxic changes in the fetal condition, it must be noted that Becker et al. demonstrated that the T/QRS baseline has no relation to the fetal condition. Since the incidence of STAN alarms is related to the fetal condition, it cannot be related to the baseline. This exactly opposes our hypothesis that the heights of the T/QRS baseline and the incidence of STAN alarms are related.

Figure 4:
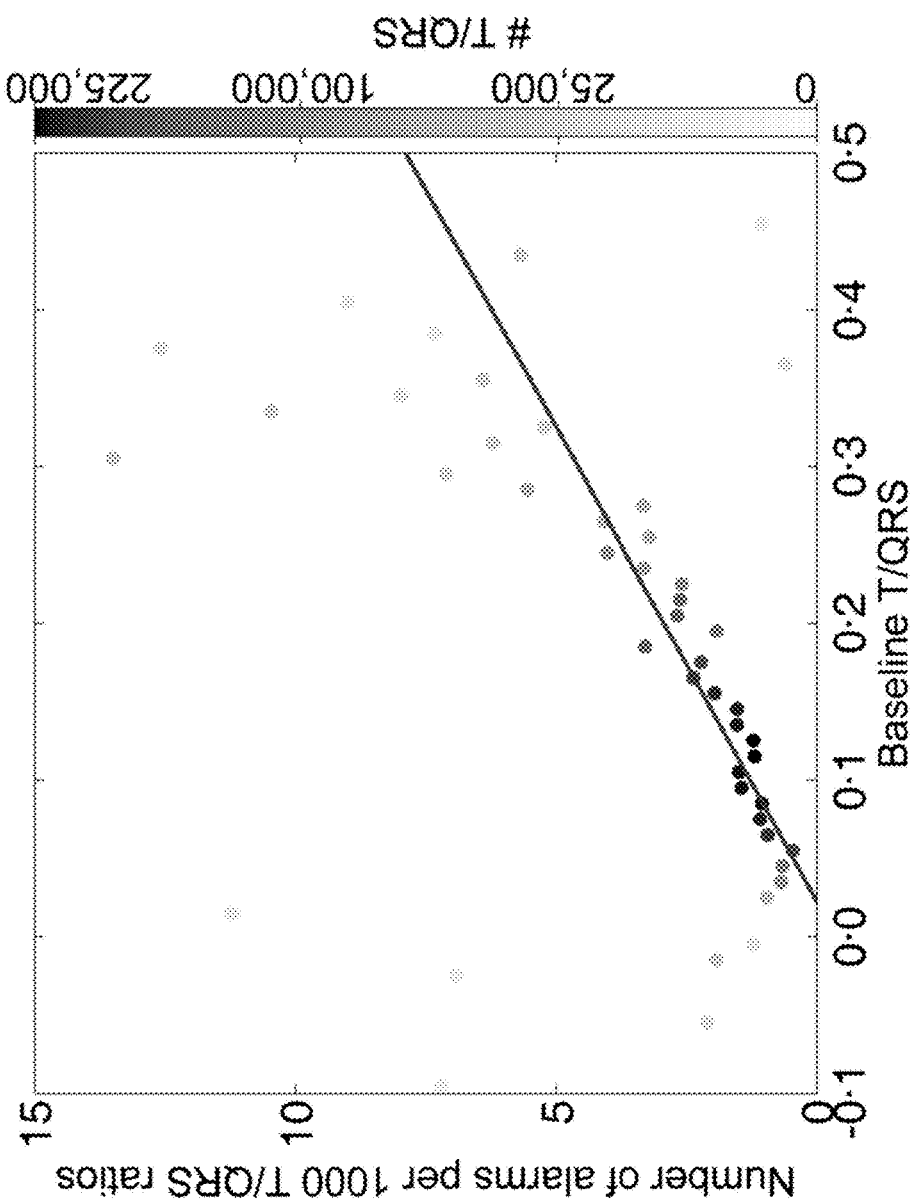
FIG. 4 shows according to an exemplary embodiment of the invention a number of STAN alarms due to a baseline T/QRS rise, presented as the number of alarms per 1000 detected T/QRS ratios and plotted as a function of the baseline T/QRS value. Patients with the same baseline T/QRS have been grouped. The darkness of the data points relates to the total number of T/QRS ratios that occurred in the group (right column in the graph). The red line represents a linear fit through the data points, and indicates an average increment of 1.65 alarms per 1000 T/QRS ratios for a baseline T/QRS rise of only 0.1. The correlation coefficient between data points and fit is 0.74 ($p<0.001$). Episodic T/QRS rises are excluded from this graph, but show a similar relation with baseline T/QRS.

We tested our hypothesis by retrospectively analysing the number of STAN events in a population of 2729 patients that all gave written informed consent. In this test population a total number of 4890 STAN alarms were reported, with only 10 cases of fetal metabolic acidosis, indicated by an umbilical cord artery blood pH<7.05 and base deficit of the extracellular fluid compartment (BDecf)>12 mmol/l. In FIG. 4, we present the number of STAN alarms as a function of the initial baseline T/QRS value. This initial baseline value is determined the same way as it is in the STAN monitor; the median of the first 20 T/QRS values that were recorded within a 20-minute window.

The results in FIG. 4 show a statistically significant increase in the number of STAN alarms with heightening of the baseline T/QRS. Considering the fact that higher baselines do not relate to higher incidence of fetal distress and considering the large patient population for which we can safely assume that the few actual cases of fetal distress can only have a marginal influence on the global trends seen, we must conclude that the presented results support our hypothesis. It has to be noted that we performed a point-by-point analysis of the "outliers" in FIG. 4, showing no relation between these outliers and (suspected) fetal distress.

Based on the previous, the incidence of STAN alarms is related to the orientation of the electrical axis of the heart, yielding some fetuses to have a relatively high probability of getting STAN alarms and some fetuses to have a relatively low probability, irrespective of their conditions. Speculating on this conclusion, we can wonder whether the main cause why fetal ST analysis in the human has not yet led to the expected improvements in fetal outcome has not been a poor transfer of earlier results from animal studies to humans, but has been the way the STAN alarm protocol was defined.
The Solution: Patient-Dependent Alarm Mechanisms In our view, the solution to the problem addressed above can be twofold. As a first solution, multiple electrodes can be used to make sure that at least one of them has the proper alignment with respect to the electrical heart axis. This approach would require the electrodes to be placed on the maternal abdomen. Unfortunately, for these recordings sufficient signal quality for reliable ST analysis cannot be guaranteed yet. A second, and probably more reliable, solution would be to generate alarms based on relative elevations of the T/QRS ratio with respect to the baseline. So rather than a baseline excess of 0.05, a baseline excess in terms of a percentage could be used. In this scenario, for patients with almost perpendicular alignment between relaxation currents and scalp lead, and thus a low baseline T/QRS, a small absolute rise in T/QRS with respect to the baseline would still yield an alarm. This would solve the problem with false alarms in the sense that hypoxia-induced ST alterations can now exceed the threshold and induce an alarm. Analogously, patients with a high baseline would have to show significant elevation above this baseline for an alarm to be raised, again potentially reducing the false alarm rate.

We tested the second solution on a group of 20 patients. Ten of these patients were born with metabolic acidosis (pH<7.05). The other ten were healthy controls, born with pH>7.20. For the alarm mechanism, we chose a relative rise in T/QRS of 70% with respect to the baseline as a threshold. This choice yielded the optimal combination of sensitivity and specificity in a ROC-curve for the threshold value; the area under the curve was 0.99. The performance of our proposed solution is presented in Table 1.

TABLE 1

Performance of detecting fetuses in distress (pH <7.05) and uncompromised fetuses (pH >7.20) by the STAN monitor (i.e. absolute threshold) and by our method (i.e. percentual threshold).

| | # correctly defined patients with pH <7.05 (sensitivity) | # correctly defined patients with pH >7.20 (specificity) |
|---|---|---|
| Alarm threshold percentage of baseline (our solution) | 9 (90%) | 10 (100%) |
| Alarm threshold absolute to baseline (STAN monitor) | 9 (90%) | 4 (40%) |
| McNemar p-value | 1.00 | 0.03 |

To further illustrate the performance of differentiating between normal and hypoxic conditions with alarms based on relative elevations of the T/QRS values, we go back to the example depicted in FIG. 3. The left panel ECG has a T/QRS rise of 89%. In the right panel, the T/QRS rise is 72%. With a threshold at 70%, both situations would have yielded a STAN alarm.

What is claimed is:

1. A method of fetal ST monitoring using an ECG monitoring system collecting a plurality of T/QRS segments of a fetus, and a data analysis computer system connected to the ECG monitoring system calculating from the plurality of T/QRS segments, wherein the improvement comprises:
    (a) determining by the computer system a first alarm of a first compromised condition of the fetus, wherein the first alarm is triggered as a first ratio of two different baseline features of the T/QRS segments exceeding a first threshold,
        wherein the first ratio is defined between B10(i) and MB20(i),
        wherein B10(i) is the median of individual T/QRS ratios within a 10-minute window preceding i,
        wherein MB20(i) is the minimum value of B20 within a 3-hour window preceding i, wherein B20 is the median of all individual T/QRS ratios within a 20-minute window preceding i,
        wherein i is minute i,
    (b) determining by the computer system a second alarm of a second compromised condition of the fetus, wherein the second alarm is triggered as a second ratio of an episodic feature between the maximum individual T/QRS in the minute i and B10(i) exceeding a second threshold; and
    (c) displaying by the computer system information of the first alarm or the second alarm which when exceeding their respective thresholds is a measure to trigger a medical intervention.
2. The method as set forth in claim 1, wherein the displaying of the alarm(s) does not rely on or does not include a cardiotocography (CTG) classification or measurement.

* * * * *